United States Patent
Chen

(10) Patent No.: US 7,350,400 B1
(45) Date of Patent: Apr. 1, 2008

(54) TEST METHOD TO MEASURE LUBRICANT MOBILITY ON A HARD DRIVE DISK

(75) Inventor: Chao Yuan Chen, San Jose, CA (US)

(73) Assignee: Samsung Electronics Co., Ltd., Suwon (KR)

( * ) Notice: Subject to any disclaimer, the term of this patent is extended or adjusted under 35 U.S.C. 154(b) by 5 days.

(21) Appl. No.: 11/525,263

(22) Filed: Sep. 22, 2006

(51) Int. Cl.
*G01N 33/26* (2006.01)
*G01N 11/00* (2006.01)
*G01B 5/18* (2006.01)
*G01B 11/22* (2006.01)

(52) U.S. Cl. .......... 73/53.05; 73/54.02; 73/150 R; 73/866; 702/166; 702/170

(58) Field of Classification Search ............ 73/53.05, 73/54.01, 54.02, 150 R, 866; 702/50, 166, 702/170
See application file for complete search history.

(56) References Cited

U.S. PATENT DOCUMENTS

| | | | |
|---|---|---|---|
| 5,559,650 A * | 9/1996 | Repphun et al. ....... 360/97.02 |
| 5,810,648 A * | 9/1998 | Jiang et al. .............. 451/285 |
| 6,246,534 B1 * | 6/2001 | Gillis et al. .............. 360/75 |
| 6,313,647 B1 * | 11/2001 | Feng et al. ............... 324/713 |
| 6,373,658 B2 * | 4/2002 | Gui et al. ............... 360/234.1 |
| 6,408,677 B1 * | 6/2002 | Suzuki ..................... 73/1.89 |
| 6,920,008 B2 * | 7/2005 | Braunstein et al. .......... 360/75 |
| 2001/0043438 A1 * | 11/2001 | Gui et al. ................ 360/236.6 |
| 2002/0015146 A1 * | 2/2002 | Meeks et al. ............. 356/73 |
| 2002/0018214 A1 * | 2/2002 | Liu et al. ................. 356/507 |
| 2002/0176185 A1 * | 11/2002 | Fayeulle et al. .......... 360/31 |
| 2004/0160604 A1 * | 8/2004 | Meeks et al. ............. 356/364 |
| 2005/0068660 A1 * | 3/2005 | Braunstein et al. ......... 360/75 |
| 2005/0132958 A1 * | 6/2005 | Leng et al. ............... 118/663 |

* cited by examiner

*Primary Examiner*—Hezron Williams
*Assistant Examiner*—David A. Rogers
(74) *Attorney, Agent, or Firm*—Ben J. Yorks; Irell & Manella LLP

(57) ABSTRACT

A method for measuring the mobility of a lubricant located on the top surface of a disk used in hard disk drives. The method includes forming one or more scribe lines in a lubricant layer of the disk. The disk is then spun by a spin stand where lubricant moves in response to the centrifugal forces of the spinning disk. The disk is removed from the spin stand and the height of lubricant that moved into the scribe line is measured to determine lubricant mobility.

6 Claims, 2 Drawing Sheets

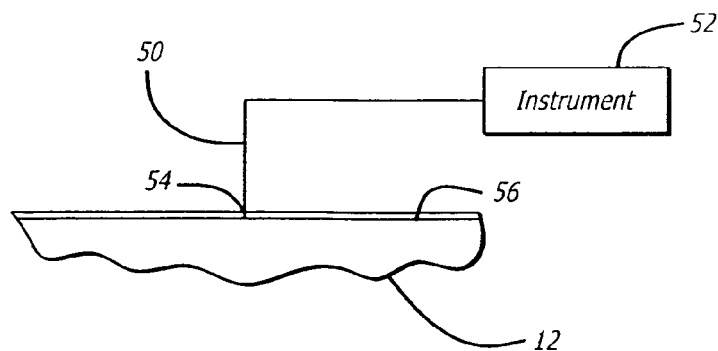
FIG. 2
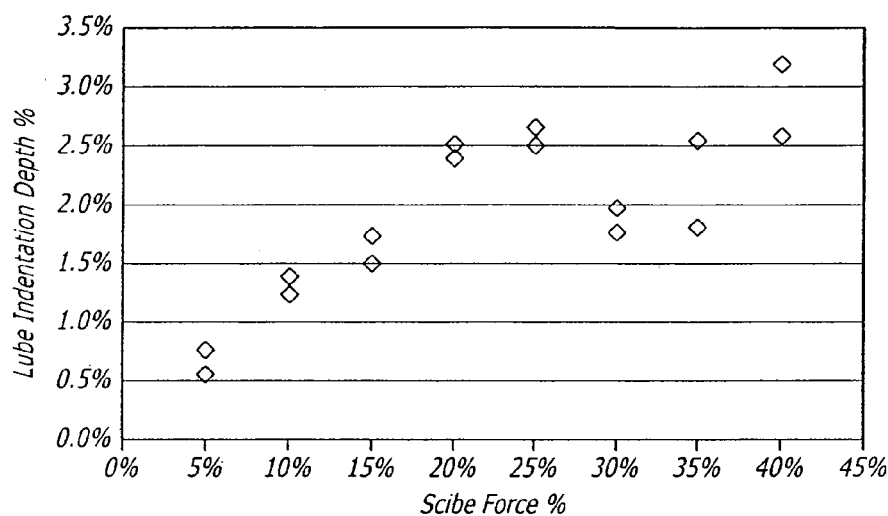
FIG. 3
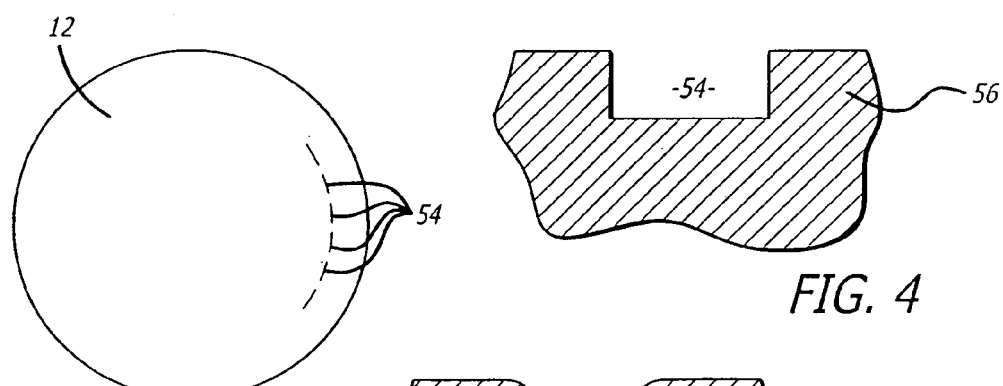
FIG. 4
FIG. 5
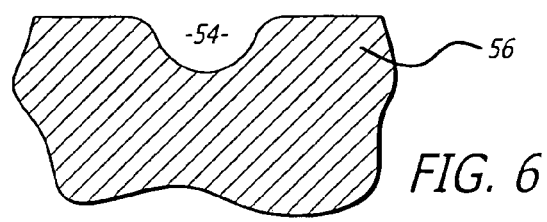
FIG. 6

TEST METHOD TO MEASURE LUBRICANT MOBILITY ON A HARD DRIVE DISK

BACKGROUND OF THE INVENTION

1. Field of the Invention

The present invention relates to measuring lubricant mobility on a surface of a disk used in hard disk drives.

2. Background Information

Hard disk drives contain a plurality of magnetic heads that are coupled to rotating disks. The heads write and read information by magnetizing and sensing the magnetic fields of the disk surfaces. Each head is attached to a flexure arm to create a subassembly commonly referred to as a head gimbal assembly ("HGA"). The HGA's are suspended from an actuator arm. The actuator arm has a voice coil motor that can move the heads across the surfaces of the disks.

The disks are rotated by a spindle motor of the drive. Rotation of the disks creates an air flow within the disk drive. Each head has an air bearing surface that cooperates with the air flow to create an air bearing between the head and the adjacent disk surface. The air bearing eliminates or minimizes the mechanical wear between the head and the disk. The height of the air bearing is commonly referred to as the flying height of the head.

The magnetic field detected by the head is inversely proportional to the flying height of the head. Likewise, the strength of the magnetic field written onto the disk is also inversely proportional to the fly height. A larger fly height will produce a weaker magnetic field on the disk.

It is desirable to minimize the fly height of the head to maximize the magnetic field strength. Consequently, disk drives have been designed to have contact or near contact between the heads and the disks. To minimize friction and damage to the disk most disk surfaces are covered with a very thin layer of lubricant.

The disks spin during operation of the disk drive. The centrifugal forces associated with such spinning motion can cause some of the lubricant to move across the disk. This movement of lubricant can vary the thickness of the disk at certain disk locations. When flying, the slider carries the air bearing force which also results in disk lubricant movement. Some head designs move out the pole-tip protrusion to reduce head disk spacing at the air gap. The higher pole-tip protrusion will increase the air bearing pressure locally near the pole-tip. The localized high pressure will generate high lube depletion forces and high lube redistribution. It is desirable to measure lubricant mobility so that the disk drives can be designed to account for movement of the lubricant.

One way to test lubricant mobility is to remove the lubricant from a portion of the disk surface, spin the disk and then measure the height of lubricant that moved into the clean area of the disk. There are various disadvantages to this approach. First, the boundary between the lubricant and the area where lubricant is removed is not crisp. It is desirable to obtain a sharp edge at this boundary so that a more accurate reading of lubricant mobility can be achieved. Second, the lubricant moves in both a radial and circumferential manner during disk spin. It is desirable to measure just the circumferential movement of the lubricant. It is difficult to measure circumferential lubricant movement with the present technique. The circumferential lube movement caused by the slider air bearing force becomes more critical at lower flying height when using a higher pole-tip protrusion. Third, only one data point can be acquired for each disk. Multiple data points require the washing, spinning and measuring of multiple disks. It would be desirable to provide a method for determining lubricant mobility that overcomes the disadvantages noted above.

BRIEF SUMMARY OF THE INVENTION

A method to determine the mobility of a lubricant located on a disk used in a hard disk drive. The method includes creating at least one scribe line on a surface of a disk that has a lubricant, spinning the disk, and measuring a lubricant that moves into the scribe line of the disk.

BRIEF DESCRIPTION OF THE DRAWINGS

FIG. 2 is a side view showing an instrument tip creating a scribe line in a surface of a disk;

FIG. 3 is a graph showing different scribe depths;

FIG. 4 is an enlarged side view showing a scribed line in the disk;

FIG. 5 is a top view showing scribe lines in the disk;

FIG. 6 is an enlarged side view showing movement of the lubricant into the scribe line.

DETAILED DESCRIPTION

Figure 1:
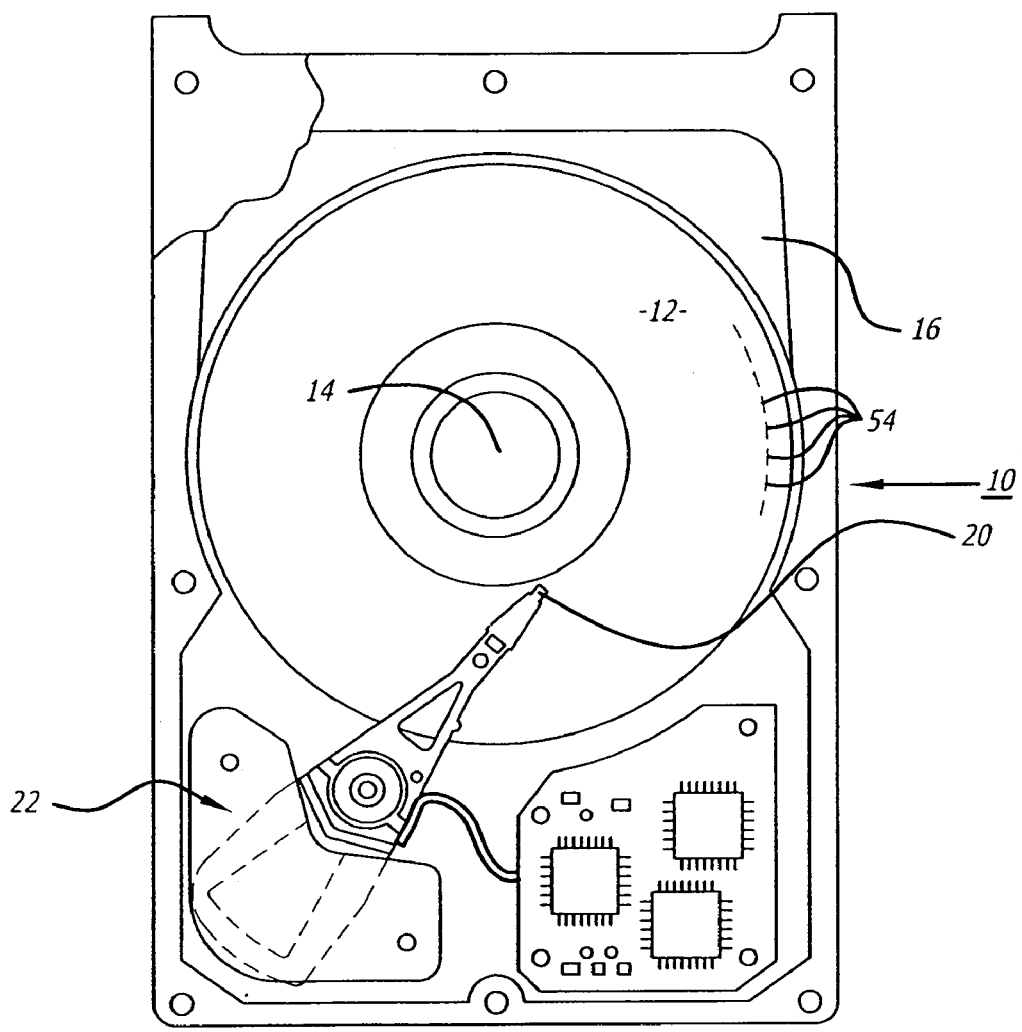
FIG. 1 is a top view of an embodiment of a hard disk drive.

Disclosed is a method for measuring the mobility of a lubricant located on the top surface of a disk used in hard disk drives. The method includes forming one or more scribe lines in a lubricant layer of the disk. The disk is then spun on a spin stand where lubricant moves in response to the centrifugal forces of the spinning disk. The disk is removed from the spin stand and the height of lubricant that moved into the scribe line is measured to determine lubricant mobility.

Referring to the drawings more particularly by reference numbers, FIG. 1 shows an embodiment of a hard disk drive 10 of the present invention. The disk drive 10 may include one or more magnetic disks 12 that are rotated by a spindle motor 14. The spindle motor 14 may be mounted to a base plate 16. The disk drive 10 may include a plurality of heads 20 located adjacent to the disks 12. The heads 20 are used to magnetize and sense the magnetic field of the disk as is known in the art. The disk drive 10 typically includes an actuator 22 that is used to move the heads 20 relative to the disk.

The disks 12 are covered with a layer of lubricant to minimize friction between the heads 20 and disk surface. During rotation of the disks 12 the lubricant may move in both a radial and circumferential direction due to the centrifugal forces associated with the spinning disk.

FIGS. 2-6 show a method for determining lubricant mobility. A tip 50 of an instrument 52 may be used to cut, at an atomic level, a scribe line(s) in both the radial and circumferential orientations 54 in a layer of lubricant 56 on the disk 12. The instrument 52 may be a product sold by KLA-Tencor of San Jose, Calif. under the designation Candela 6100 Optical X-Beam Surface Analyzer that is equipped with a diamond tip. The instrument 52 can measure surface depths by measuring changes in reflectivity of the disk surface. The scribe line(s) 54 may have different depths as shown by the graph in FIG. 3. The scribe lines may have a width no greater than 10 microns. The small width allows for improved resolution when measuring the movement of the lubricant.

After the scribe line 54 is formed, the disk 12 is placed on a spin stand (not shown). By way of example, the disk 12 may be placed on a Vena spin stand tester and rotated at 20,000 revolutions per minute. Rotation of the disk causes lubricant to move across the disk. As shown in FIG. 6, lubricant 56 moves into the scribe line 54. The height of the lubricant that moves into the scribe line 54 can be measured with the instrument 52. The height of the lubricant is used to determine lubricant mobility. By way of example, the height of lubricant within the scribe line can be used as a lubricant mobility index.

As shown in FIG. 4, scribing the disk with the tip 50 creates a sharp edge at the boundary between the lubricant and the area with no lubricant. This allows for more accurate readings on the amount of lubricant that flows into the scribed area. If the boundary had a slope, the slope would have to be measured and accounted for, or there would be an inaccurate measurement of lubricant flow.

As shown in FIG. 3, a plurality of scribe lines 54 may be formed in the disk. The multiple scribe lines 54 can be measured with a single scan of the instrument 52. This allows for the measurement of multiple data points from a single disk. This is to be distinguished from the prior art where different disks would have to be washed, spun and measured to obtain multiple data points.

The scribe lines 54 can be located at the same radial location on the disk 12. This allows for multiple data points for circumferential movement of the lubricant. Circumferential movement within a scribe line 54 can be determined by measuring lubricant height across the length of the scribe line 54.

When spinning the disk, the head flying can be coupled with the spinning disk to study lube movement under the slider air bearing force and disk spinning centrifugal force. The ratio of these two forces can be adjusted by adjusting the disk RPM and pole-tip protrusion. By adjusting the ratio of the two forces, the lube spreading mechanisms can be fully understood under each lube movement force.

The spin test also could be conducted in different environmental conditions to study the lube mobility property at different temperature and humidity conditions.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method to determine the mobility of a lubricant located on a disk used in a hard disk drive, comprising:
    creating at least one scribe line in a lubricant of a lubricant layer on a surface of a disk, the scribe line having a predetermined depth;
    spinning the disk;
    measuring a height of lubricant that moves into the scribe line of the disk; and
    determining lubricant mobility based on the predetermined depth of the scribe line and the measured lubricant height.

2. The method of claim 1, wherein there are created a plurality of scribe lines in the lubricant layer on the surface of the disk.

3. The method of claim 2, wherein the scribe lines have different depths.

4. The method of claim 2, wherein the scribes lines are located at approximately a same radius of the disk.

5. The method of claim 1, wherein the scribe line has a width no greater than 10 microns.

6. The method of claim 1, wherein the circumferential mobility of the lubricant is measured.

* * * * *